DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED APRIL 3, 1973

909 O.G. 5

T909,003

PAN GRANULATION OF UREA

Gordon C. Hicks, 3307 19th Ave., and Melvin M. Norton, Virginia Shores, Rte. 1, both of Sheffield, Ala. 35660

Filed Mar. 22, 1972, Ser. No. 236,882

**Int. Cl. C07c *127/00***

U.S. Cl. 260—555

1 Sheet Drawing. 9 Pages Specification

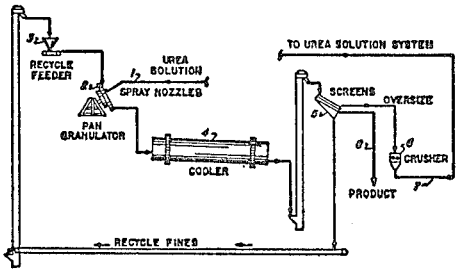

FLOW DIAGRAM OF PILOT PLANT FOR PRODUCTION OF GRANULAR UREA

A process for producing in a pan granulated large and closely sized urea granules eminently suitable for sulfur overlay and the like, wherein a concentrated solution of about 98–99 percent concentration is sprayed into the pan granulator (as in McCamy et al., U.S. 3,165,395) but wherefrom the subsequent drying step and equipment is eliminated. Alternatively, more highly concentrated urea feed may be utilized (as in Thompson et al., U.S. 3,408,169) without the requirement of mechanical deflection inwardly of the solid particles across the face of the pan, and wherein the spray headers need not necessarily be located in the upper right hand quadrant thereof. The temperature in the pan is maintained from 200° F. upward to 250° F., but preferably from about 200° to 210° F. About 3 pounds of recycled undersize are required per pound of product.

Novel techniques developed for producing the large, smooth, spherical urea granules include (1) use of large, closely sized urea granules as startup recycle and continuing to recycle only material slightly smaller than the desired product, (2) screening the product of a narrow size range, e.g., −5 +7 mesh, (3) dissolving dust from the dry dust collectors and from the oversize crusher in the urea solution, rather than returning it dry, (4) carefully regulating the urea spray pressure to the pan. With these techniques, successive thin layers of urea were built up on the surfaces of the recycled material. Control of granulation was so precise that only about 1 percent of the pan product was oversize.

PAN GRANULATION OF UREA
Filed March 22, 1972
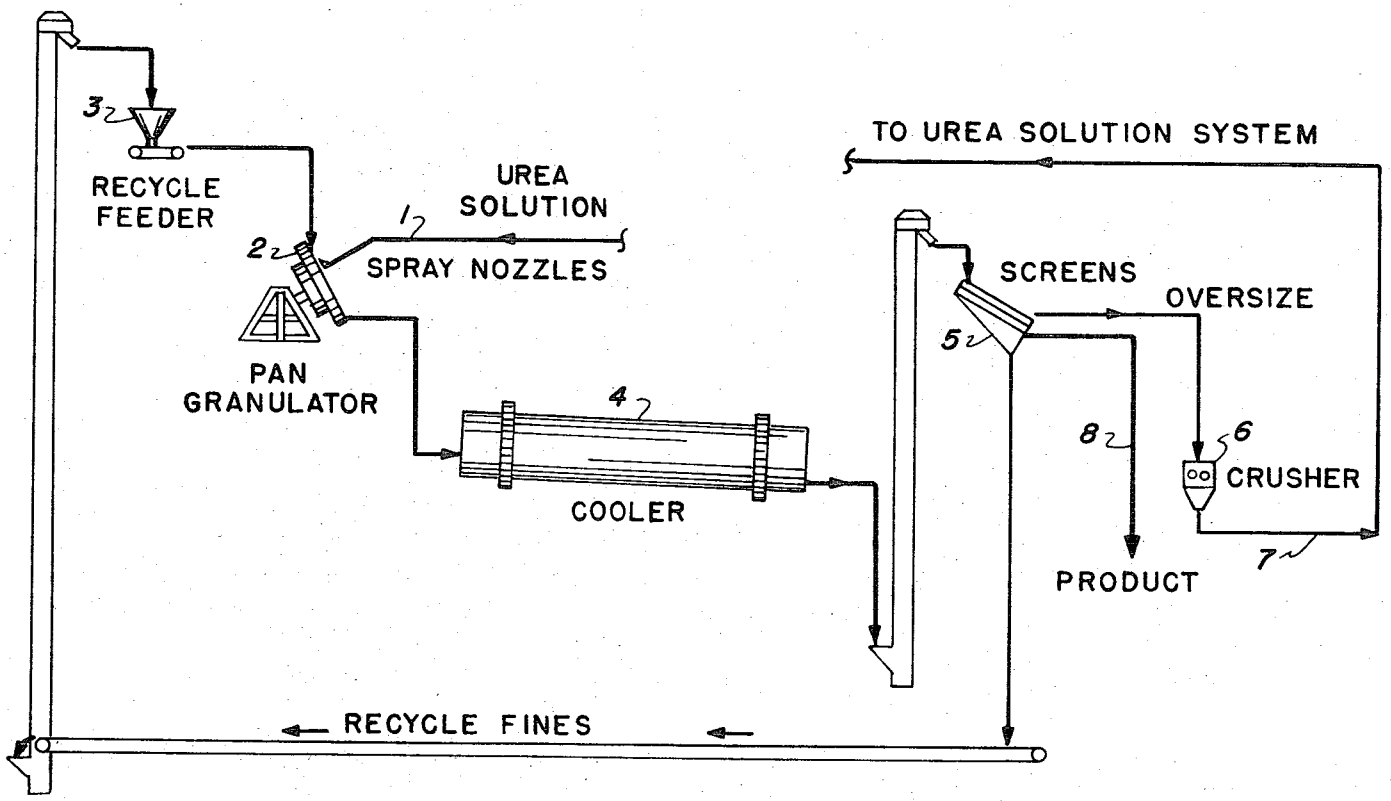
FLOW DIAGRAM OF PILOT PLANT FOR PRODUCTION OF GRANULAR UREA